United States Patent [19]

Coggins et al.

[11] 4,383,042
[45] May 10, 1983

[54] PROCESS FOR DETECTING SOFT SPOTS IN ALUMINUM

[75] Inventors: Dolphus L. Coggins, St. Louis; Eugene R. Fannin; John Gumbelevicius, both of St. Louis County, all of Mo.

[73] Assignee: McDonnell Douglas Corporation, St. Louis, Mo.

[21] Appl. No.: 284,004

[22] Filed: Jul. 16, 1981

[51] Int. Cl.³ .................... G01N 33/20; G01N 19/08
[52] U.S. Cl. .......................................... 436/5; 73/104; 252/960
[58] Field of Search .................. 23/230 R, 230 C; 73/104; 436/5

[56] References Cited

U.S. PATENT DOCUMENTS

| | | | |
|---|---|---|---|
| 2,391,522 | 12/1945 | Slunder | 23/230 R |
| 3,652,224 | 3/1972 | Johnson et al. | 73/104 X |
| 3,652,225 | 3/1972 | Coffin, Jr. et al. | 73/104 X |
| 3,652,226 | 3/1972 | Coffin, Jr. et al. | 73/104 X |
| 4,067,751 | 1/1978 | Pistulka | 73/104 X |

Primary Examiner—Michael S. Marcus
Attorney, Agent, or Firm—Gravely, Lieder & Woodruff

[57] ABSTRACT

A process and compositions for detecting improperly processed areas in heat treated aluminum are disclosed. A solution containing an acid or a base and an oxidizing agent and, if desired, a color enhancing ingredient is applied to an aluminum object to produce a color difference between those areas of the surface of the object which have been properly hardened and the areas resulting from improper heat treatment. The solution can be applied to the aluminum by brushing, swabbing, immersion or spraying. The acid or base in the solution attack the aluminum surface so that the oxidizing agent in the solution can react with the aluminum to produce the aforementioned color differential.

11 Claims, No Drawings

PROCESS FOR DETECTING SOFT SPOTS IN ALUMINUM

BACKGROUND OF THE INVENTION

This invention is related to the art of treating aluminum parts to detect visually those localized areas which have been degraded by improper processing. Such areas can be found in heat treated aluminum alloy products as a result of variations in quenching from the solution treating temperature, overaging of nonuniform precipitates or by overheating during subsequent processing. What actually results is that local areas in a particular part have lower hardness and mechanical properties than other areas of the part. Parts with such conditions must be detected so that an aircraft or other device is not built from material with inferior mechanical properties.

These local areas of hardness or strength differences can be detected if each square inch of a component is inspected by standard methods such as hardness or electrical conductivity testing. But such extensive testing is uneconomical so a visual detection method is preferred. One known method for visually checking the entire surface of an aluminum part is by anodizing. In an anodizing process, an electric current is used with the part being one of the terminals to produce a coating on the aluminum. Such a surface treatment reveals improperly processed areas as differing in color from the properly hardened areas.

Using an anodizing process to detect these areas of hardness differences has several disadvantages. Among these are the high cost of anodizing, and the long processing time involved. Also, a particularly significant problem is the loss of metal resulting from removing the anodized coating after inspection. This sometimes results in dimensional changes on close tolerance parts to such an extent that the parts become nonacceptable. Another disadvantage of anodizing is that on nonmachined parts, such as forged or rolled surfaces, the anodizing process sometimes produces erratic results, resulting in missing the detection of localized variations in strength and hardness.

Among the other advantages of the present invention is that the cost to detect local areas of strength and hardness difference in aluminum parts is reduced by two-thirds or more, and the time is reduced from about 40 minutes to 10 minutes or less. The metal loss is minimal and the film can be stripped in 10–15 seconds after inspection.

A further advantage of the new process is that the film does not interfere with penetrant inspection, whereas an anodic film must be removed before penetrant inspection. Thus, a processing step is eliminated because the film can be easily removed during the normal cleaning required to remove the penetrant. In penetrant inspection, a part is checked for cracks or flaws by applying a composition which contains a visible dye or fluorescent material and is flowed into the flaws. Typical patents showing this type testing are U.S. Pat. No. 3,436,959 and U.S. Pat. No. 3,418,078.

This invention, unlike anodizing, gives a high degree of sensitivity and reliability making it possible to detect degraded areas in machined or forged/rolled articles.

Accordingly, a principal objective of the present invention is to provide a process for detecting improperly processed areas in aluminum without going through the anodizing technique. Another objective of the present invention is to provide a process for detecting local hardness/strength variations in aluminum parts by applying a solution containing an oxidizing agent and an acid or base to produce a visually perceivable color difference between properly and improperly processed areas of the aluminum. These and other objectives and advantages will become apparent hereinafter.

SUMMARY OF THE INVENTION

The present invention comprises treating an aluminum alloy part with a solution containing an acid or a base which will react with the aluminum alloy, plus an oxidizing agent, which reacts with the aluminum alloy to produce color differences between properly hardened areas and areas of lower hardness and lower mechanical properties. The solution may be applied to the aluminum part by swabbing, brushing, spraying or by immersion.

DETAILED DESCRIPTION

While the precise mechanism which causes the present invention to function is not completely understood, it is believed that the functioning of the solution, which selectively stains those areas in aluminum which have been degraded through improper processing, results from the use of a base or acid which removes any pre-existing aluminum surface. While this is occurring, the oxidizing agent, through a series of complex and not totally understood oxidation-reduction reactions with the aluminum, produces in the degraded areas of the aluminum a darker color than that imparted to those parts of the aluminum which were properly processed. This selective staining is believed to be due at least in part to differences in electrochemical properties created within the material, resulting from metallurgical characteristics. It further is believed that this factor also plays a role in producing different redox reactions, all of which combine to result in distinct color differences between areas of proper hardness and other areas.

There are a number of bases and acids which can be used in the treating composition. The only critical factor is that the base or acid must react with aluminum and aluminum alloy and it must dissolve the ever present aluminum oxide film from the surface of the aluminum part. Suitable acids include $H_2SiO_2$, $HF$, $H_2SO_4$, and $HCl$. Nitric acid is not suitable because it does not attack aluminum. Among the bases which could be used are $NaOH$, $KOH$, and $Ca(OH)_2$.

The suitable oxidizing agents include $K_2Cr_2O_7$, $Cr_2O_3$, $NaNO_3$, etc. The oxidizing agent usually produces color on its own and a dye is not necessary as a coloring agent. However, it may be desirable to add a color enhancing ingredient to certain compositions, and for this purpose $Na_2S_4$ or any other suitable color enhancing ingredient is suitable.

The oxidation reaction is a function of time, temperature and the strength of the oxidizing agent and the acid or base. The operating temperature may be varied from ambient to close to the boiling point of the treating composition. The higher the temperature, the faster the reaction goes. Similarly, a fast acting solution can be made by increasing the concentration of base or acid. If desired, surfactants and etching inhibitors may be added as needed for particular applications.

A suitable alkaline solution is formulated as follows:
 5% NaOH

10% $Na_2S_4$
1% $K_2Cr_2O_7$
84% $H_2O$

A suitable acid solution is as follows:

10% $H_2SiO_2$
1% $Cr_2O_3$
89% $H_2O$

Generally, a mild oxidation reaction is preferred so as to minimize damage or dimensional changes in the part. If the oxidizing reaction is too severe, some of the benefits of the present process are eliminated.

When anodizing is used, a film 0.1–1.0 mils in thickness is formed, and when this is stripped approximately one-half this much of the part surface is removed. In parts with close tolerance, this can result in the part being rejected. Using this present process, the film thickness is only 0.01 mils and has minimal effect on the tolerance of the part when it is removed.

EXAMPLE NO. 1

(A) An aluminum part which has been heat treated is immersed into a non-etch alkaline cleaner to remove any organic contamination. The cleaner is a typical industrial cleaner such as Turco 4090, but any equivalent cleaner can be used.

(B) The part is rinsed with tap water.

(C) The part is immersed into a typical aluminum deoxidizer to produce a chemically clean surface. The typical deoxidizer is Amchem 17-7, but any equivalent deoxidizer can be used.

(D) The part is rinsed with tap water.

(E) The part is then immersed into the detection solution for 1.5–2.0 minutes. The detection solution contains 10% $H_2SiO_2$, 1% $Cr_2O_3$, and 89% $H_2O$. If immersion of the part is inconvenient or not desirable for any reason, detection solution may be applied by swabbing, spraying, or brushing in such a manner that the article is wet for 1.0–1.5 minutes.

(F) The part is then rinsed with tap water.

(G) The part is allowed to dry at ambient temperature.

(H) The dried part is examined visually for local variations in color which indicate differences in metallurgical structure. The colors may vary with alloy and their shading with immersion time, but generally, properly processed areas will vary from a light brown to a dark brown metallic color while degraded areas will be indicated by a gray to dark gray color.

(I) Upon completion of the inspection, the film is removed from the part by immersing the part into a typical deoxidizer solution for 15–20 seconds.

(J) Alternately, the part is taken directly from the visual examination procedure to a penetrant inspection station where it is treated as follows:
 1. apply typical penetrant dye,
 2. dry/develop penetrant dye, and
 3. inspect.

(K) The final step is to clean the penetrant solution and the oxidized film from the part by immersion into typical deoxidizer solution for 15–20 seconds, rinse, and dry.

What is claimed is:

1. The method of detecting whether an article consisting principally of aluminum has been degraded by improper processing so that it contains regions which are of lowered hardness and mechanical properties than surrounding regions of desired hardness, which comprises the steps of:
 (a) cleaning the surface of an article consisting principally of aluminum;
 (b) applying to the cleaned surface a film forming solution which contains (1) an agent which attacks the aluminum to dissolve aluminum oxide from said surface and which is selected from the group consisting of acids and bases and (2) an inorganic oxidizing agent which forms said film, said oxidizing agent having a composition different from said agent which attacks the aluminum;
 (c) rinsing the surface with water after the solution of step (b) has been in contact with the surface for a time sufficient to form said film on said surface;
 (d) drying the article; and
 (e) examining said surface visually to determine the presence of local variations in color of said film which identify any of said regions which are of lowered hardness and mechanical properties.

2. The method of claim 1 wherein the solution contains an ingredient to enhance the color of improperly processed areas of the aluminum part.

3. The method of claim 1 wherein the solution is acidic.

4. The method of claim 1 wherein the solution is basic.

5. The method of claim 1 including the subsequent step of treating the aluminum article with a penetrant test material without first removng the oxidized film.

6. The method of claim 5 including the steps of cleaning the article to remove the penetrant test material and the oxidized film at the same time.

7. The method of claim 1 wherein the oxidizing agent is selected from the group consisting of $K_2Cr_2O_7$, $Cr_2O_3$, and $NaNO_3$.

8. The method of claim 3 wherein the acid is selected from the group of $H_2SiO_2$, HF, $H_2SO_4$, and HCl.

9. The method of claim 4 wherein the base is selected from the group of NaOH, KOH, and $Ca(OH)_2$.

10. A method of detecting areas in an article consisting principally of aluminum that have been degraded by improper processing comprising the steps of:
 (a) cleaning the surface of the aluminum articles;
 (b) applying to the cleaned aluminum article a film forming solution consisting essentially of 5% NaOH, 10% $Na_2S_4$, 1% $K_2Cr_2O_7$ and 84% $H_2O$;
 (c) rinsing the surface with water after the solution of step (b) has been in contact with the surface for a time sufficient to form said film on said surface; and
 (d) observing the treated article for differently colored areas indicating areas of different metallurgical properties which are characterized by lowered hardness and mechanical properties.

11. A method of detecting areas in an article consisting principally of aluminum that have been degraded by improper processing comprising the steps of:
 (a) cleaning the surface of the aluminum article;
 (b) applying to the cleaned aluminum article a film forming solution consisting essentially of 10% $H_2SiO_2$, 1% $Cr_2O_3$ and 89% $H_2O$;
 (c) rinsing the surface with water after the solution of step (b) has been in contact with the surface for a time sufficient to form said film on said surface; and
 (d) observing the treated article for differently colored areas indicating areas of different metallurgical properties which are characterized by lowered hardness and mechanical properties.

* * * * *